United States Patent [19]

Poindexter

[11] Patent Number: 5,466,153
[45] Date of Patent: Nov. 14, 1995

[54] PROP FOR USE IN DENTISTRY AND ORAL SURGERY

[76] Inventor: Forrest R. Poindexter, 7729 Jewelweed Ct., Springfield, Va. 22152

[21] Appl. No.: 213,729

[22] Filed: Mar. 16, 1994

Related U.S. Application Data

[63] Continuation-in-part of Ser. No. 824,159, Jan. 22, 1992, abandoned.

[51] Int. Cl.⁶ .................................................. A61C 5/00
[52] U.S. Cl. .................................... 433/140; 433/138
[58] Field of Search .................... 433/31, 93, 136, 433/138, 140

[56] References Cited

U.S. PATENT DOCUMENTS

| | | | |
|---|---|---|---|
| 765,537 | 7/1904 | Abbott | 433/138 |
| 802,408 | 10/1905 | Rowe | 433/138 |
| 3,722,101 | 3/1973 | Via, Jr. | 433/140 |
| 4,975,057 | 12/1990 | Dyfnermark | 433/93 |
| 4,992,046 | 2/1991 | Sharp | 433/93 |

OTHER PUBLICATIONS

"Shur–Prop" article, May 1984.

*Primary Examiner*—Cary E. O'Connor
*Attorney, Agent, or Firm*—Glenna Hendricks; Stephen Gates

[57] ABSTRACT

The invention is a device for use as a prop to hold the mouth open which consists essentially of a bite block with an elongated portion that is deflected to provide a turn of about 180° so that the elongated portion extends around the outside of the cheek with the end of the extension pointing backward from the mouth to form a handle by which the bite block is held in position.

17 Claims, 4 Drawing Sheets

PROP FOR USE IN DENTISTRY AND ORAL SURGERY

This application is a continuation-in-part of U.S. Ser. No. 07/824,159, filed Jan. 22, 1992, which is now abandoned.

FIELD OF THE INVENTION

The subject invention is a prop for holding the mouth open to be used during oral surgery and during dental treatment and repair. The device is particularly valuable when caring for an uncooperative or incompetent patient.

BACKGROUND OF THE INVENTION

Many prop devices, with or without suction means, are available to the dentist and oral surgeon. However, an adaptation of the relatively simple prop disclosed in U.S. Pat. No. 2,220,674 continues to be used. That patent discloses and claims a device with a cheek-engaging convex portion having a pair of spaced diverging trough portions that formed a U-shaped trough section on which the teeth rested. Devices fitting this general description continue to be sold and used. These devices are simple in design and relatively inexpensive. However, if the patient is unable or unwilling to cooperate due to age, mental disability, or response to medication, the dental practitioner or an assistant will have difficulty getting the device to remain in place. Attempts to hold the device in place may result in impaired visibility of and access to the mouth. Furthermore, the person holding the device in place is subject to injury from biting or contact with devices used by the dental practitioner.

U.S. Pat. No. 3,924,333 discloses a dental appliance for evacuating debris and liquid from the mouth. The device is a bite block with an opening in the transverse direction through the block to permit passage of a tube to provide for evacuation of the oral cavity. The device is used with an attached dam. No handle for holding the device is seen.

U.S. Pat. No. 4,167,814 discloses a bite block having a means for attachment of a suction tube that bends to provide a U-shaped portion with suction holes to evacuate fluid from the oral cavity. No handle extends outside the mouth for holding the device in place.

U.S. Pat. No. 4,192,071 discloses a dam connected to a bite block through which there passes a tube for suctioning the oral cavity. The device is quite complex and lacks a handle for holding the device in place.

U.S. Pat. No. 4,975,057 discloses a bite block with openings to admit suction tubing. The device has an aperture in the transverse direction from the exterior of the bite block though the block into the oral cavity.

A prop called the SHUR-PROP was previously sold by MYDENT of Plainview, N.Y. The prop consisted of a bite block with a clip having an anchoring protrusion that fits into a receiving hole in the lateral surface of the block. The block differs from the instant invention since the block can not be readily adjusted to fit farther back into the mouth without pressure which pulls the lips backward as the cheek retractor is clipped to the cheek.

The device that enjoys continued use is the bite block of U.S. Pat. No. 2,220,674.

DETAILED DESCRIPTION OF THE INVENTION

The purpose of the invention is to provide an improved device for supporting the jaws in the open position during dental surgery and treatment in a manner that will facilitate use of instruments by the dental practitioner and will protect the assistant from being bitten or injured by instruments in the patient's mouth during dental procedures while improving the comfort of the patient undergoing treatment. The device is simple and economical enough to occasion wide use. Because the device is inexpensive, it can be sold as a disposable unit. Use of such disposable devices avoids expense of cleaning and spread of infection.

During dental procedures it is often difficult for the patient to relax while maintaining the mouth in an open position. The device of the invention makes it much easier for the patient to relax his jaw muscles during prolonged dental procedures. A handle part which is formed by an elongated portion that protrudes from the anterior face of the block is deflected to provide a turn of about 180° with the portion deflected being sufficiently extended beyond the turn to enable the practitioner having average adult hand size to grasp the deflected portion with at least two fingers to hold the bite block in place.

The device of the invention can also be used to prop the mouth open during application of medications to the back of the mouth and the throat or during collection of samples from that region. It would also be possible to use the device during lavage of the throat. The device is also useful to care givers attempting to give oral hygiene to patients who are unable to cooperate with the care giver. Because the device is symmetrical, only one device is needed since it can be used in either side of the mouth. The devices could be provided for each patient for use with his other oral hygiene equipment.

The device of the invention consists essentially of a bite block with an elongated portion that extends from the anterior aspect of the block so that the elongated portion is deflected to provide a turn of about 180° to act as a handle portion. The elongated portion extends around the outside of the cheek with the end of the extension pointing backward from the mouth to form a handle by which the bite block is held in position. Because of the shape and position of the handle, the view of the dental practitioner is not obstructed by the hand holding the bite block in place. Because the extension protrudes from the anterior aspect or face of the block it is possible to adjust the depth of the block within the mouth. Such adjustment is not possible if there is a protrusion from the lateral aspect of the block which holds the block in position. Furthermore, instruments introduced into the mouth do not come into close proximity with the hand holding the bite block in place. Since sharp instruments and needles can be a source of infection, the instant invention is useful in preventing spread of infection to care givers.

Figure 1:
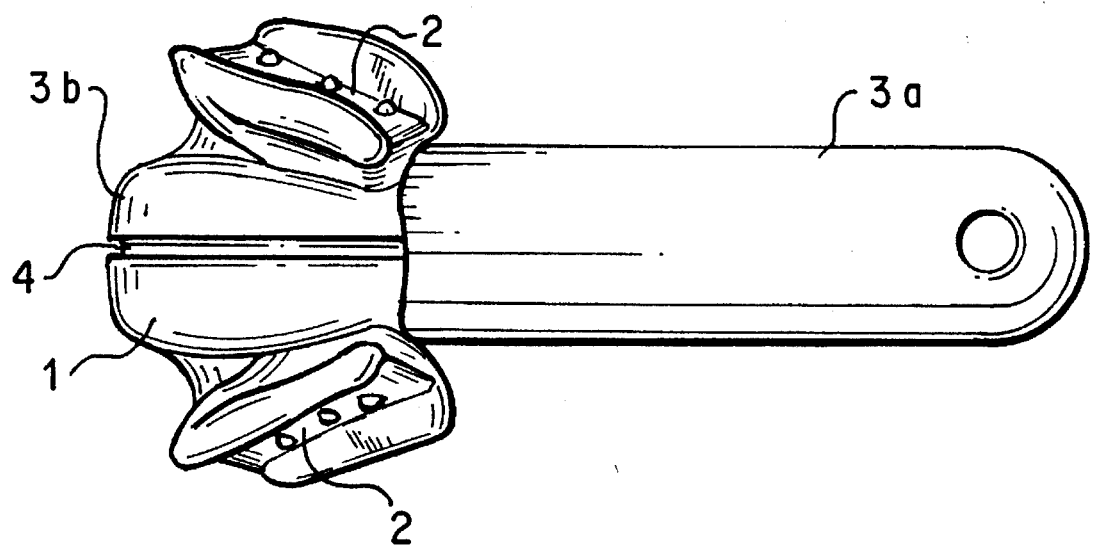
FIG. 1 is a view of the prop device from the aspect which is medial when the device is in place.
Figure 2:
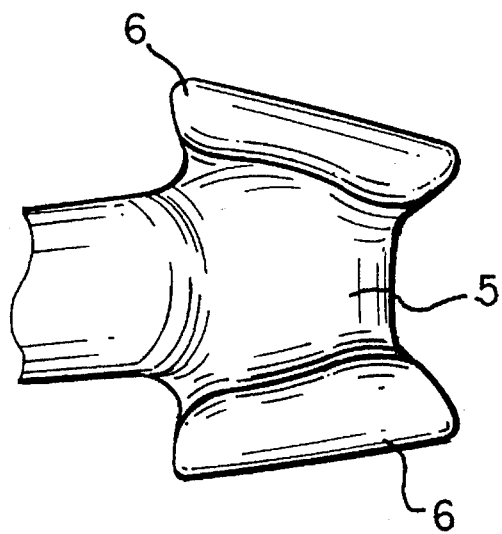
FIG. 2 is a view of the block from the aspect which is lateral when the device is in place.

Referring to the drawings, FIG. 1 is a view of the device from the medial aspect, that is, the view from the side that is positioned against the tongue when the block is in place. The surface (1) against which the tongue will rest when the block is in use (also referred to as the medial face or surface) may have a groove (4) which can hold a suction tube. The block provides two bite surfaces (2) which may have ridges or other irregularities which increase efficiency of the grip when the block is in place. The handle (3a) is formed by the elongated portion extending from the anterior surface (3b) of the block and bent back over onto itself. FIG. 2 is a view of the block from the lateral aspect, that is, the view from the side that is positioned against the cheek when the block is in use (5) (also referred to as the lateral face or surface). Extensions from the medial and lateral faces of the block provide flanges (6) on either side of the bite surfaces which help to hold the block in place.

Figure 3:
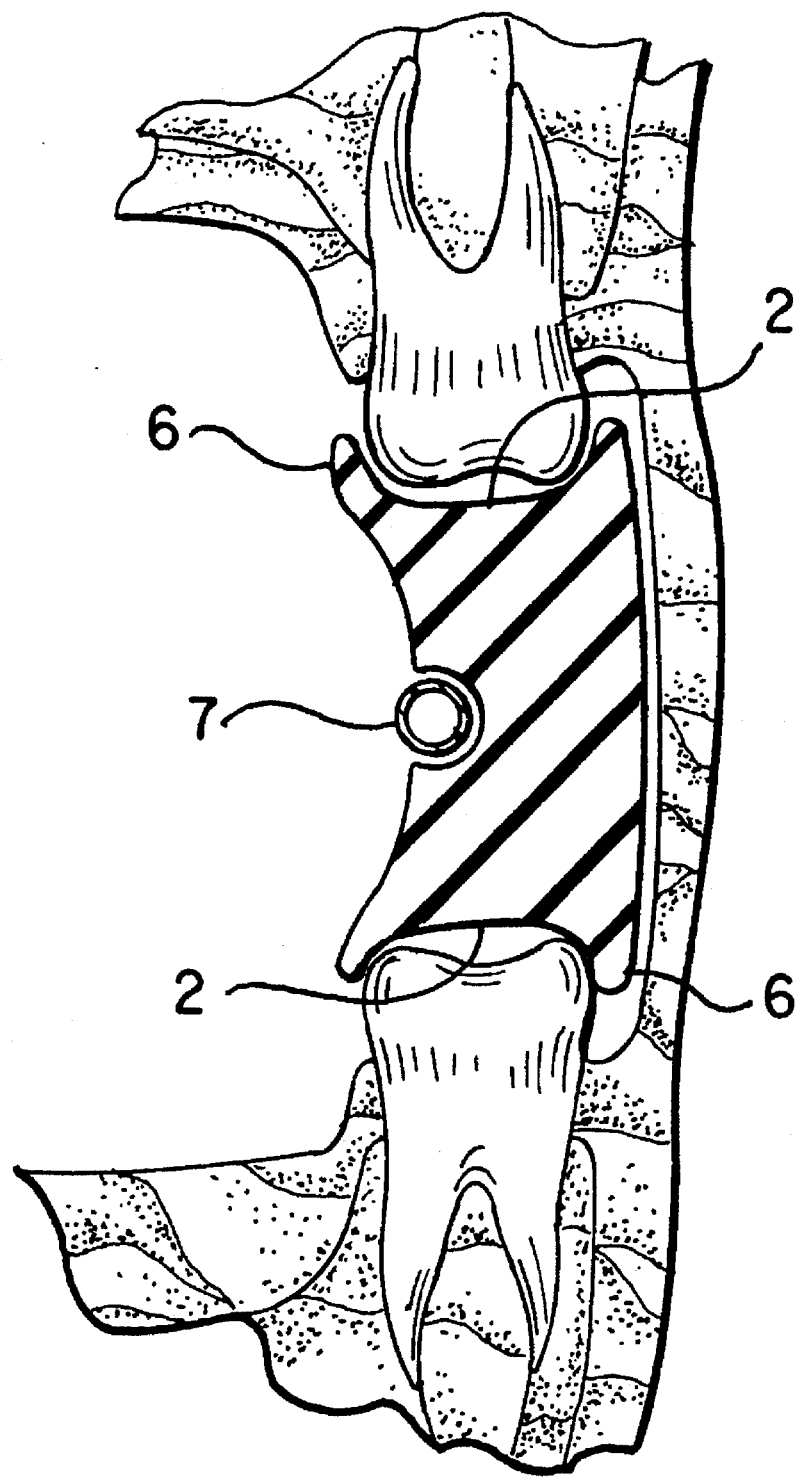
FIG. 3 is a view through the cross section of the prop when the block is in place between the jaws.
Figure 4:
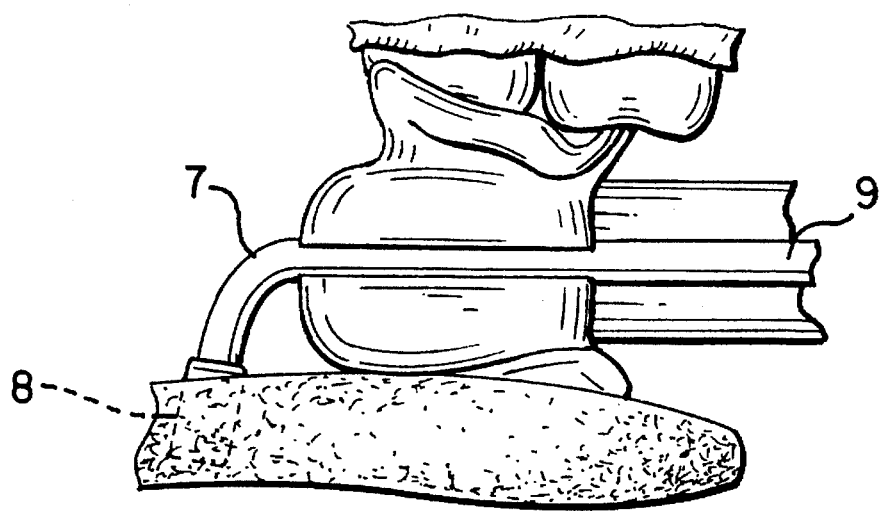
FIG. 4 is a medial view of the block in place.

FIG. 3 is a cross section of the block in place between the jaws. The ridges (6) hold the teeth against the bite surfaces (2) and the suction tube (7) is in position. FIG. 4 provides a medial view of the block with the suction tube (7) wherein the tip of the suction tube (8) is resting against the floor of the side of the mouth against the tongue (9). While a suction tubing may be an integral part of the block, it is often more convenient simply to have a groove into which the suction tubing fits. This allows the dental practitioner to position the tubing as needed for the individual patient. Alternatively, the bite block may have an opening in the transverse direction though which the suction tubing is passed or the opening may be a hole running from anterior to posterior through the block and may also pass through the forward part of the elongated portion.

Figure 5:
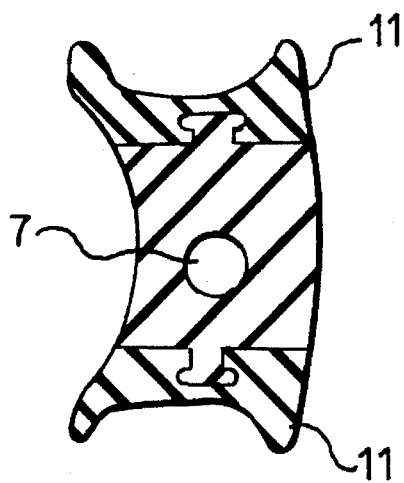
FIG. 5 shows a cross section of the bite block with replaceable bite surfaces.
Figure 5A:
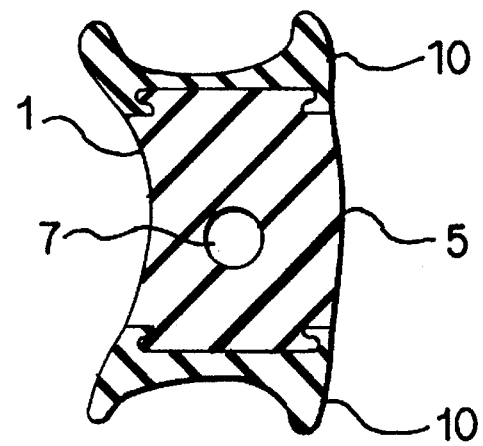

FIG. 5 depicts a cross section of the block having replaceable bite surfaces (10 and 11) The cap 10 is a rubber or rubber-like material that is a cap that fits over a protrusion of the block. The cap 11 fits over a smaller protrusion. While not shown in the drawings, the bite body may have the indentation and the nipple may be on the bite cap. Any means by which a rubber cap may be fitted over a more rigid body would be appropriate. The suction tube (7) passes through a hole positioned anterior to posterior though the bite block.

Figure 6:
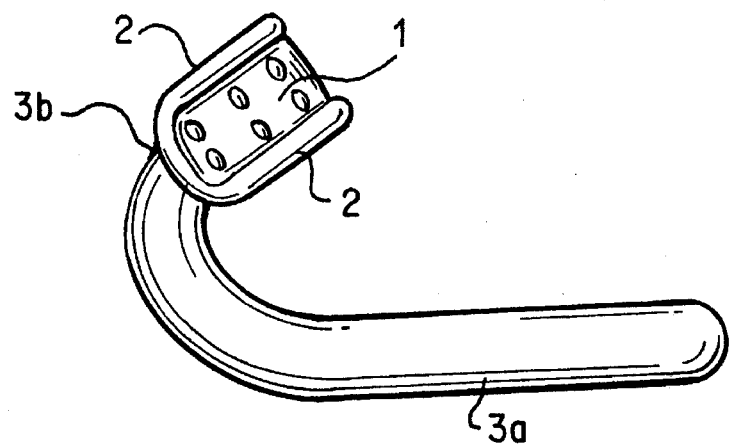
FIG. 6 is a view of the prop device showing the handle extending from the anterior surface.

FIG. 6 depicts the device from another angle showing lateral surfaces (2), an anterior surface (3b) a medial surface (1), a handle (3a) extending from the anterior surface of the block and bent at about a 180° angle.

Figure 7:
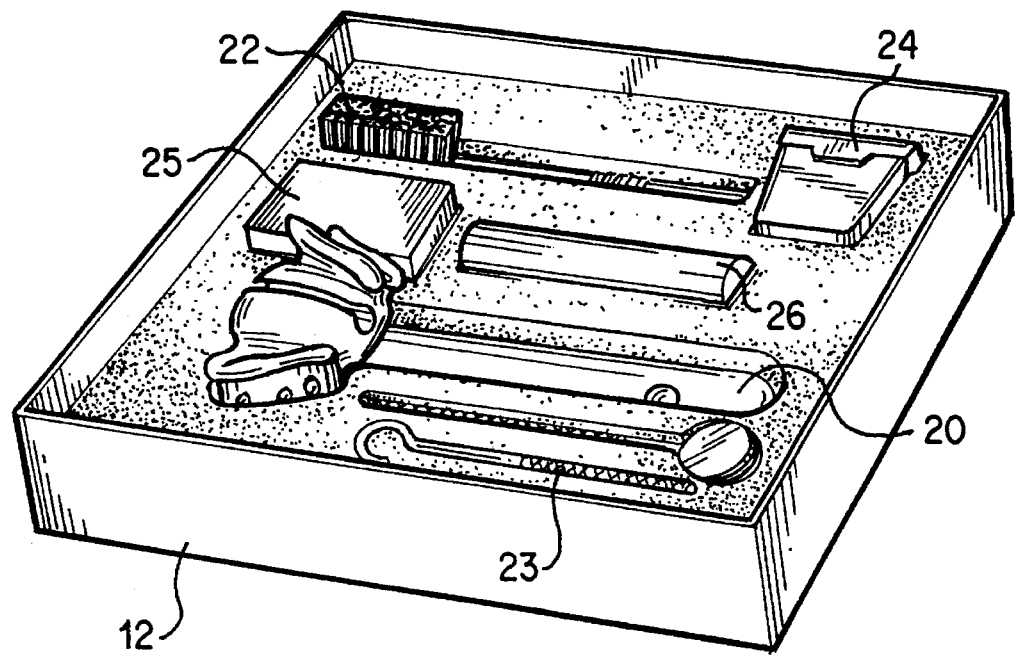
FIG. 7 shows a kit for use in administering dental care.

FIG. 7 depicts a kit (12) containing therein the bite block of the invention (20) tooth brush (22), swabs (23), dental floss (24) and a dentifrice (25) and a disinfectant (26).

The suction tubing, when part of the block, may pass through the body of the bite block alone through a lateral surface or may pass through both the handle and the bite block from the front. However, the use of a separate tube attached through the groove gives the practitioner greater latitude to adjust the suction tubing to meet the needs of the particular situation. While the drawings show a bite block having a groove with a tube lying within the groove, the suction tubing may be placed through a transverse aperture in the mouth block, with the tubing passing between the lips and transversely through the mouth block.

The devices of the invention can be made in several sizes for use with different patients. Because the blocks are symmetrical, they may be used on either side of the mouth. The devices may be used along with the traditional rubber dams or other isolation procedures used during dental treatment.

While the bite block can be made of any material that will provide sufficient support for the jaw, preferred materials allow some deforming upon biting by the patient. Such materials include resilient plastic or rubber materials. A particularly preferred material is polystyrene which permits initial deformation to conform to the bite of the particular patient. It is also possible to use a combination of materials such as a metal core covered with resilient materials such as plastics or rubbers (natural or synthetic) of varying rigidity. When the devices are to be reused, the devices should be made of material that can be easily cleaned and sterilized. The method of sterilization may be chemical or physical (thermal, irradiation, ultrasound, etc.) and will depend on the equipment available and the material used to make the bite block. For reusable devices, a metal core covered with silicone rubber-like material or other similar material may be used.

Semi-rigid, deformable materials that deform easily upon initial contact are particularly useful for practice of the invention. Such materials deform upon initial contact because the cells are compressed in the immediate vicinity of the pressure to render the material more dense in the area compressed. Continued or additional deformation is resisted since the denser material is more rigid after deformation. Hence, once in place, the material compressed is quite resistent to further deformation. Styrenes, silicones, polyurethanes and similar materials can be made particularly for this purpose.

The prop may be constructed of a strong, long-lasting substance such as metal or rigid plastic with detachable, replaceable bite surfaces of softer, deformable materials for long-term use for patients that can not cooperate with health care workers. The device could be made with or without the groove for the suction tube. However, the device without the groove having a smooth surface would be more appropriate where suction was not needed, since a smooth surface would be easier to clean and sterilize.

The device may be provided with appropriate brushes and/or swabs, dental floss and compositions for oral care such as cleaning pastes or powders, lemon oil, and oral rinses such as Listerine or fluoride rinses in a kit form. Such a kit could be provided for bedside use.

I claim:

1. A prop comprising a bite block having an anterior surface and two bite surfaces and an elongated portion that extends from said anterior surface of said bite block wherein said elongated portion is deflected to provide a turn of about 180°.

2. The prop of claim 1 wherein the medial aspect of the block has a groove to accommodate suction tubing.

3. The prop of claim 2 wherein the bite block is made of semi-rigid material.

4. The prop of claim 1 wherein the lateral side of the block that is positioned against the cheek is convex in shape.

5. The prop of claim 1 wherein the bite block is made of a semi-rigid deformable material.

6. The prop of claim 5 wherein the bite block is made of polyurethane.

7. The prop of claim 1 wherein the bite block is made of metal covered with silicone rubber.

8. The prop of claim 1 wherein the bite surfaces are made of a material that is softer than the block.

9. The prop of claim 8 wherein said bite surfaces are detachable and replaceable.

10. The prop of claim 1 wherein said prop has a hole running transversely though the bite block.

11. The prop of claim 1 wherein said prop has a hole through the bite block in the anterior-posterior direction for acceptance of suction tubing.

12. A method of holding the mouth open during dental treatment or mouth care by inserting into the mouth a bite block having an anterior surface and two bite surfaces and having an elongated portion that extends from said anterior surface of said bite block wherein said elongated portion is deflected to provide a turn of about 180°.

13. A kit for administering dental hygiene wherein said kit contains compositions for oral care and a prop comprising a bite block having an anterior surface and two bite surfaces and an elongated portion that extends from said anterior surface of said bite block wherein said elongated portion is deflected to provide a turn of about 180°.

14. A kit of claim 13 containing a dentifrice.

15. A kit of claim 13 containing a disinfectant.

16. A kit of claim 13 containing a tooth brush and dental floss.

17. A kit for use in dental surgery wherein said kit contains compositions for oral care and a prop comprising a bite block having an anterior surface and two bite surfaces and an elongated portion that extends from said anterior surface of said bite block wherein said elongated portion is deflected to provide a turn of about 180°.

* * * * *